United States Patent [19]

Hsieh

[11] Patent Number: 5,727,041
[45] Date of Patent: Mar. 10, 1998

[54] METHODS AND APPARATUS FOR REDUCING PARTIAL VOLUME IMAGE ARTIFACTS

[75] Inventor: Jiang Hsieh, Waukesha, Wis.

[73] Assignee: General Electric Company, Milwaukee, Wis.

[21] Appl. No.: 747,639

[22] Filed: Nov. 13, 1996

[51] Int. Cl.[6] .................................................. A61B 6/03
[52] U.S. Cl. .................................. 378/4; 378/8; 378/901
[58] Field of Search ........................... 378/4, 8, 15, 901

[56] References Cited

U.S. PATENT DOCUMENTS 5,241,576  8/1993  Lonn ............................................ 378/19

Primary Examiner—David P. Porta
Assistant Examiner—David Vernon Bruce
Attorney, Agent, or Firm—John S. Beulick; John H. Pilarski

[57] ABSTRACT

The present invention, in one form, is a method for improving image quality in Computed Tomography systems by using a partial volume artifact estimation algorithm. In accordance with one embodiment of the algorithm, an object of interest is scanned to generate image data. The image data is segmented into low attenuation data and high attenuation data. A gradient image is generated for two adjacent slices of the image data. The gradient image is then forward projected and squared. The squared gradient image is an estimation of partial volume artifacts in the image data, and therefore is removed from the image data.

20 Claims, 2 Drawing Sheets

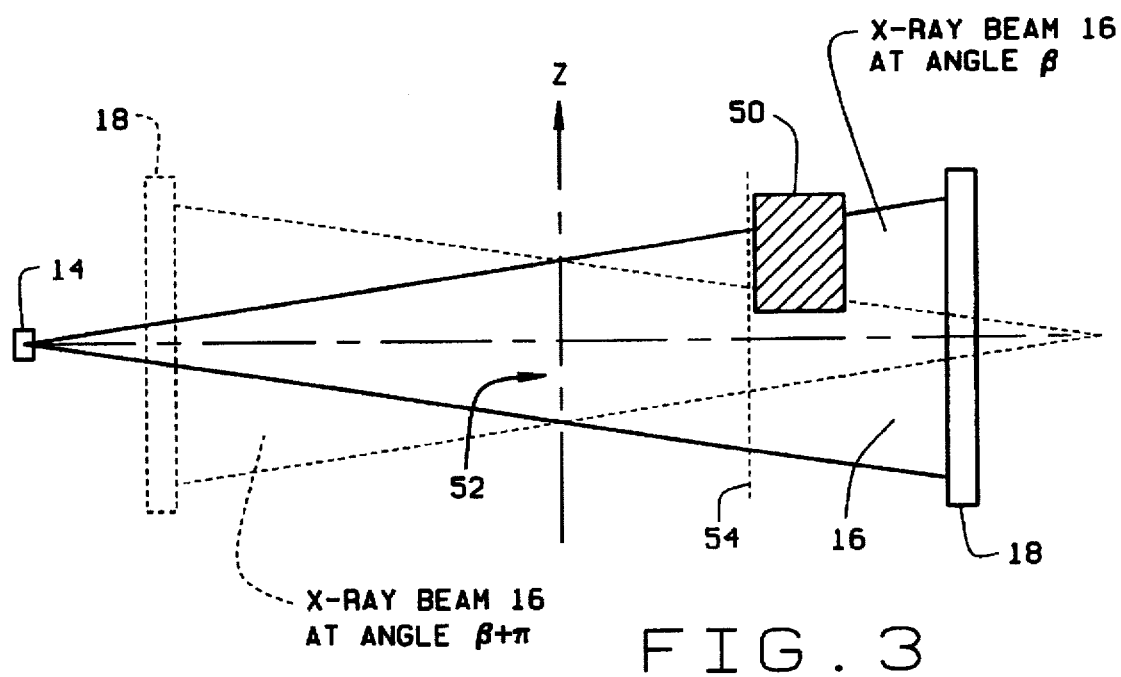
FIG. 3
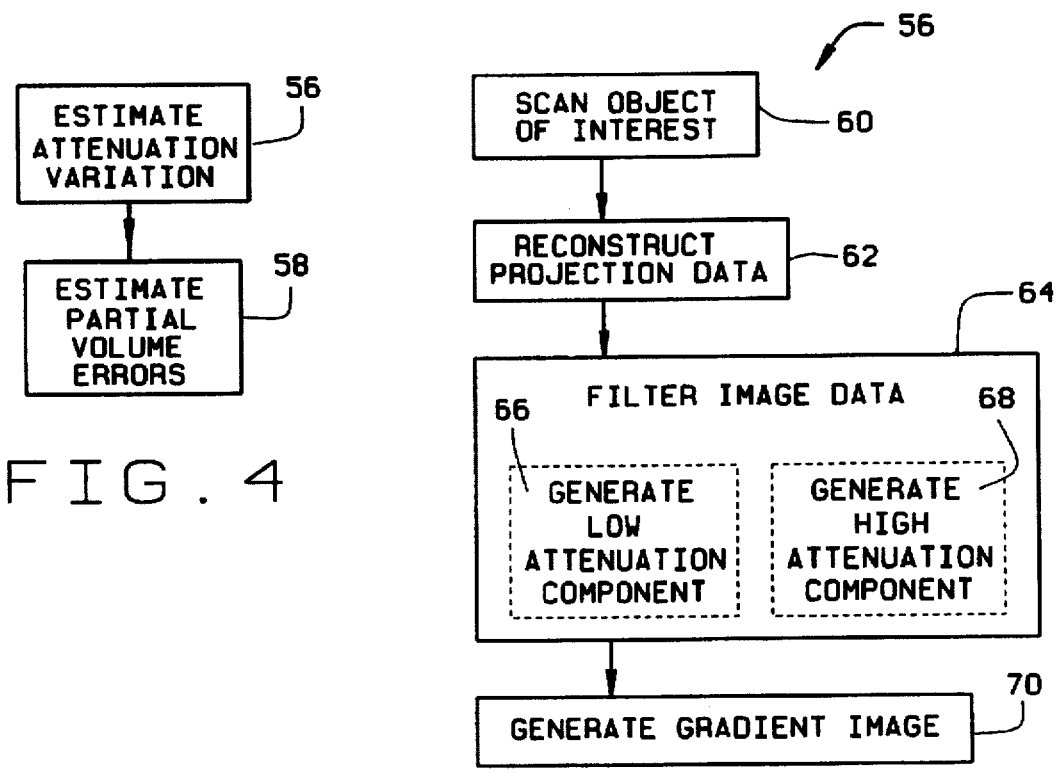
FIG. 4
FIG. 5

METHODS AND APPARATUS FOR REDUCING PARTIAL VOLUME IMAGE ARTIFACTS

FIELD OF THE INVENTION

This invention relates generally to computed tomography (CT) imaging and more particularly, to reducing partial volume image artifacts in an image reconstructed from scan data.

BACKGROUND OF THE INVENTION

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object.

One method for reconstructing an image from a set of projection data is referred to in the art as the filtered backprojection technique. This process converts the attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed. In addition to reduced scanning time, helical scanning provides other advantages such as improved image quality and better control of contrast.

In helical scanning, and as explained above, only one view of data is collected at each slice location. To reconstruct an image of a slice, the other view data for the slice is generated based on the data collected for other views. Helical reconstruction algorithms are known, and described, for example, in C. Crawford and K. King, "Computed Tomography Scanning with Simultaneous Patient Translation," Med. Phys. 17(6), November/December 1990.

During scanning, the x-ray beam is known to spread along a z-axis to form a "scan plane". For each image slice, the object to be imaged often only partially intrudes on the scan plane. Specifically, the object is only partially subjected to the x-ray beam, thus causing inconsistencies in the projection data. When reconstructing an image for a particular slice, these inconsistencies generate incorrect CT numbers, streaks, and other artifacts in generated images. As the slice thickness is increased, the likelihood of partial intrusion increases. The image errors created by partial intrusion are often referred to as "partial volume artifacts".

To reduce partial volume artifacts, operators typically must select slices of sufficiently small thickness to ensure constant attenuation characteristics across the slice, i.e., to ensure that the object does not partially intrude on the scan plane. However, thin slices typically require significantly long scanning times and x-ray tube cooling delays. Conversely, thicker slices are preferred for improving x-ray photon flux. Therefore, it is desirable to reduce partial volume artifacts while permitting thicker slices.

Another known method of reducing partial volume artifacts includes altering x-ray source collimators during a scan. For example, a 10 mm collimator which provides a slice thickness of 10 mm may be used when scanning a region with few bony structures. However, when scanning a region with multiple bony structures, a 3 mm collimator which provides a slice thickness of 3 mm, may be used. This method is both time consuming and cumbersome. Furthermore, this method is neither practical nor efficient when scanning adjacent differing regions.

Yet another known method of reducing partial volume artifacts includes interpolating multiple slices of data. Particularly, axial variations in adjacent slices are estimated. The slice to be imaged is then sub-divided into three sub-slices. The estimated variations are then applied to the sub-slices to reduce partial volume artifacts in the slice to be imaged. This method, however, is not always accurate. This method also is cumbersome.

In yet another known method, several thin slices are combined to generate a single image. Each thin slice is selected to be small enough to avoid partial volume artifacts. The images are combined, or summed, in either the projection domain or the image domain. Although this method is relatively successful in reducing partial volume artifacts, this method significantly reduces the CT system efficiency and patient throughput.

It is desirable, of course, to reduce partial volume artifacts without significantly reducing CT system efficiency. It also is desirable to reduce partial volume artifacts without adversely affecting image resolution.

SUMMARY OF THE INVENTION

These and other objects may be attained by methods and apparatus which substantially remove partial volume artifacts from a desired image of an object reconstructed using scan data without reducing image resolution. In accordance with one embodiment, the object is scanned to generate projection data for at least two slices of the object. The projection data then is processed to generate image data for each slice. The image data for each slice is then filtered to remove low attenuation regions. Such filtering is performed by segmenting the data into two components. One component is referred to as the low attenuation component and the other component is referred to as the high attenuation component. Such segmentation can be performed using grey-scale thresholding.

After the image data for each slice is filtered as described above, a gradient image is generated using the image data for the two slices. The gradient image is then forward projected and squared to estimate partial volume error. The estimated partial volume error is then removed from the image to be displayed prior to displaying such image.

Using the above-described algorithm, partial volume artifacts are reduced without reducing CT system efficiency. In addition, the image resolution is maintained.

BRIEF DESCRIPTION OF THE DRAWINGS

FIG. 3 is a schematic illustration of an x-ray source, a detector, and a partially intruded object of interest.

FIG. 4 illustrates a sequence of steps executed in accordance with one embodiment of the present invention.

FIG. 5 illustrates a sequence of steps executed during attenuation variation estimation in accordance with one embodiment of the present invention.

DETAILED DESCRIPTION OF THE DRAWINGS

Figure 1:
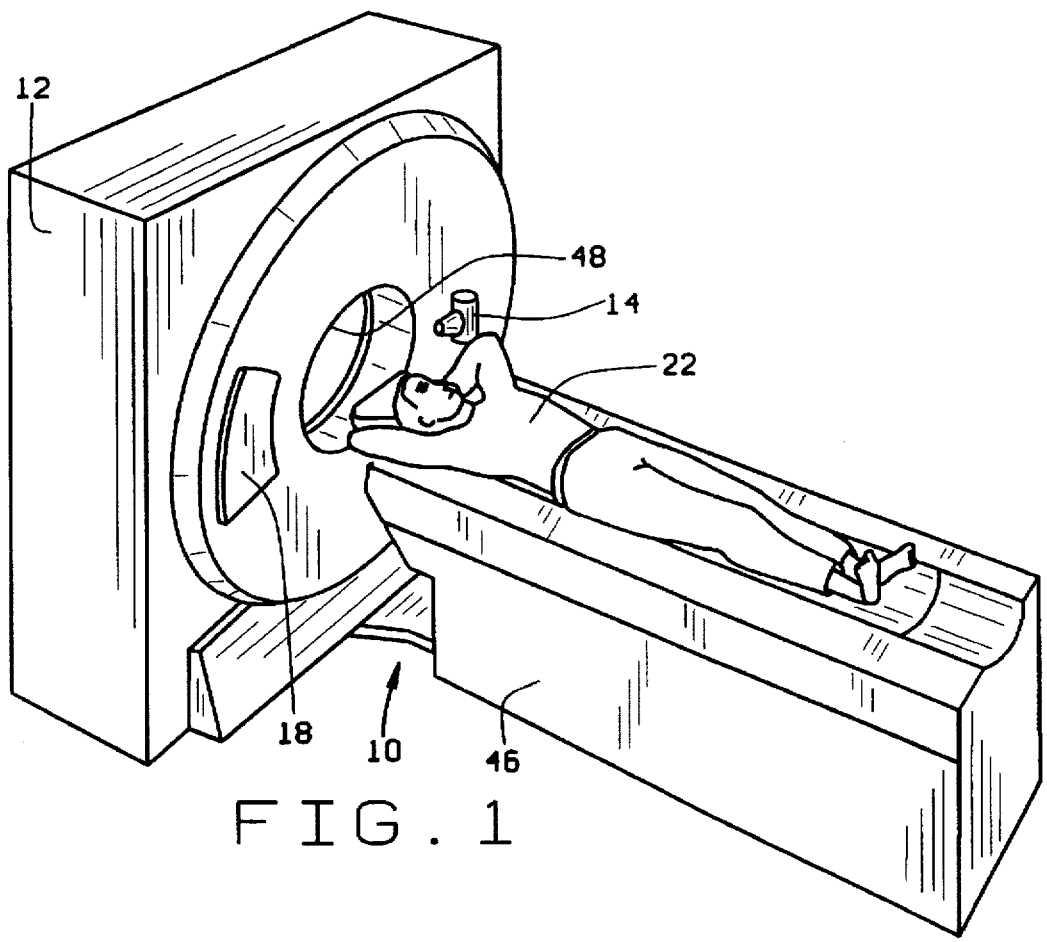
FIG. 1 is a pictorial view of a CT imaging system.
Figure 2:
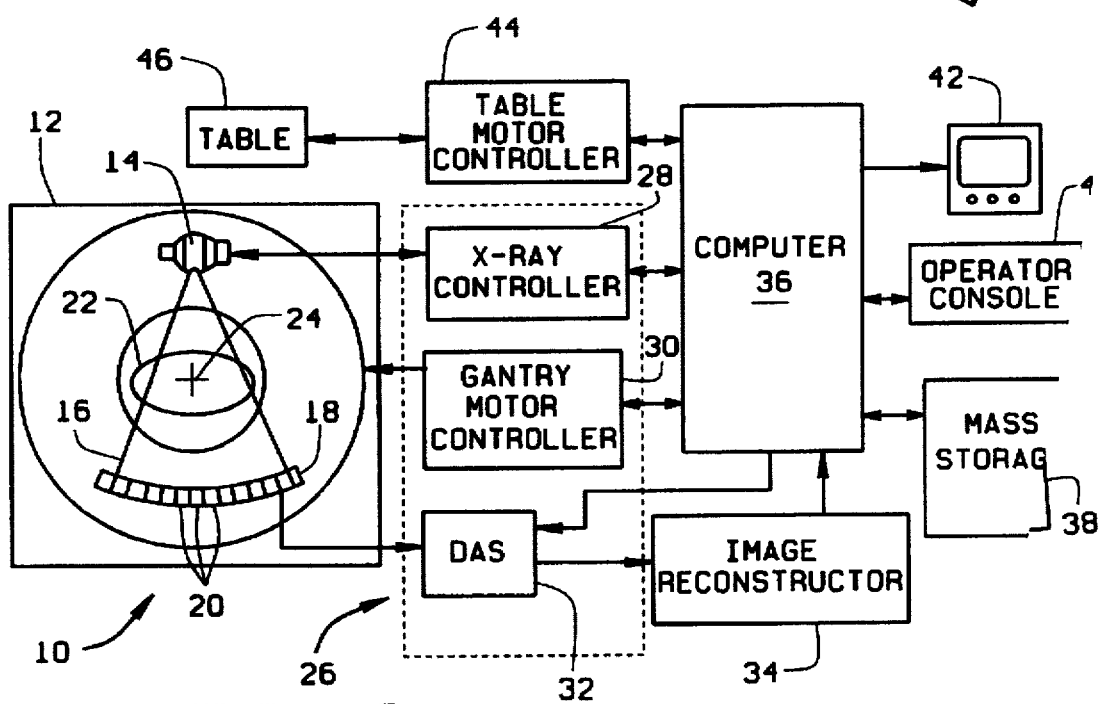
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. X-ray beam is collimated by a collimate (not shown) to lie within in an X-Y plane of a Cartesian coordinate system and generally referred to as an "imaging plane". Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a amble motor controller 44 which controls a motorized amble 46 to position patient 22 in gantry 12. Particularly, table 46 moves portions of patient 22 through gantry opening 48.

The following discussion which describes reducing image artifacts sometimes refers specifically to an axial scan. The artifact reduction algorithm, however, is not limited to practice in connection with only axial scans, and may be used with other scans, such as helical scans. It should be further understood that the algorithm would be implemented in computer 36 and would process, for example, image data stored in mass storage 38. Alternatively, the algorithm could be implemented in image reconstructor 34 and supply filtered image data to computer 36. Other alternative implementations are, of course, possible.

FIG. 3 is a schematic illustration of x-ray source 14, detector array 18, and a partially intruded object of interest 50. Object of interest 50 typically is a portion of patient 22 being scanned. X-ray source 14 projects x-ray beam 16 at an angle β towards object of interest 50 and detector array 18. X-ray beam 16 typically diverges about an iso-center 52 along a z-direction to form a "scan plane" 54. The divergence of x-ray beam 16 impinging detector array 18 is referred to herein as "slice thickness".

As shown in FIG. 3, x-ray beam 16 only passes through a portion of object of interest 50, i.e., object of interest 50 "partially intrudes" on scan plane 54. As explained above, this partial intrusion causes errors and artifacts in slice images of object of interest 50. In addition, the extent of partial intrusion is angularly dependent. More specifically, at an angle β+π, object of interest 50 is nearer to x-ray source 16, and thus a smaller portion of object of interest 50 partially intrudes scan plane 54 (shown in phantom in FIG. 3). Such angular dependence causes inconsistencies in projection data acquired during a scan of object of interest 50. These inconsistencies, as explained above, cause partial volume artifacts in resulting images of the object of interest.

Object of interest 50 typically has an attenuation distribution $\mu(x,y,z)$, and is scanned with a slice thickness h. Assume that the z-axis is orthogonal to the scanning plane, and that the x-ray flux emitted from x-ray source 14 is approximately uniform in z. The average line integral of the attenuation of object of interest 50 over slice thickness h can be expressed by:

$$P_{av} = \frac{1}{h} \int_0^h P(z) dz \qquad (1)$$

where P(z) is a true line integral of the attenuation distribution through a plane at height z, and is expressed as:

$$P(z) = \int \mu(x, y, z) ds. \qquad (2)$$

A measured line integral, $P_m$, can be approximated by the following equation:

$$P_m = P_{av} - \frac{1}{2h} \int_0^h [P(z) - P_{av}]^2 dz. \qquad (3)$$

From equation (3), it is shown that the magnitude of partial volume error is approximately proportional to the square of the variation in the attenuation distribution of object of interest 50 in z. It also is shown that the amount of partial volume error is related to slice thickness, h. Furthermore, it is shown that where object of interest 50 comprises two different materials, a maximum partial volume error occurs where each material occupies approximately half of the space in z.

As explained above, known methods for reducing partial volume artifacts, or partial volume error, include decreasing slice thickness, h, used in scanning. While such methods are generally successful, they also increase the time necessary to scan object of interest 50, and introduce delays, such as tube cooling delay. Such methods, therefore, also reduce patient throughput.

In accordance with one embodiment of the present invention, partial volume artifacts are reduced by estimating the attenuation variation in object of interest 50, and removing partial volume artifacts from an image in accordance with the estimated attenuation variation. Particularly, and referring to FIG. 4, the present algorithm estimates 56 the attenuation variation in object of interest 50, and estimates 58 partial volume errors, or partial volume artifacts, in accordance with such attenuation variation estimation 56. The estimated partial volume errors are then subtracted to generate a partial volume corrected image.

Referring to FIG. 5, and for attenuation variation estimation 56, object of interest 50 is scanned 60 with an axial scan to obtain projection data. Particularly, object of interest 50 is scanned 66 to obtain projection data for at least two slices. Reconstruction 62 is then performed to generate image data for each slice. With respect to image reconstruction, many image reconstruction algorithms are known and some of the known algorithms are implemented in commercially available CT machines. The present algorithm could be implemented in connection with many of such reconstruction algorithms and is not directed to, nor limited to practice with, any one particular image reconstruction algorithm.

Subsequent to axial reconstruction 62, the resulting image data is filtered 64 to remove low attenuation regions. This filtration 64 is performed by segmenting the image data into two segments. Specifically, a low attenuation component 66 and a high attenuation component 68 are generated. This segmentation is performed, in one embodiment, using grey-scale thresholding. Grey-scale thresholding refers to the process of comparing CT numbers with a predetermined range, i.e., a threshold, and assigning each CT number to a particular component based on whether the respective CT number is above or below the threshold. Further details regarding grey-scale thresholding are set forth in U.S. Pat. No. 5,400,377, Artifact Reduction Method For Tomographic Image Reconstruction Using Cross-Plane Rays, which is assigned to the present assignee. The threshold, for example, may be 200 HU, and each portion of the image data having a CT number lower than the threshold may be set to zero. The thresholding may be performed, for example, by computer 36.

After filtering 64 the image data, a gradient image is generated 70. Particularly, and for at least two adjacent slices, a gradient image is generated to identify variations of object of interest 50 across the slices. The higher the difference between the adjacent slices, the more likely that partial volume artifacts will be present in a final image of object of interest 50.

After identifying variations across the slices, partial volume artifacts are estimated 58 in accordance with Equation (3). Particularly, and as explained above, partial volume artifacts are approximately proportional to the square of the attenuation variation in object of interest 50. Accordingly, partial volume artifacts of object of interest 50 may be estimated by forward projecting the gradient image and squaring such forward projections. Forward projecting techniques are known, and many such techniques may be used in connection with the present algorithm. Since partial volume artifacts typically are low frequency in nature, the smoothing nature attendant to forward projection is believed not to detract from the capabilities of the present algorithm.

The estimated partial volume artifacts are then removed from an image prior to displaying such image. Specifically, assume that a desired image of object of interest 50 is to be displayed. The gradient image projections are processed to generate an "artifact only" image. The artifact only image includes only the estimated partial volume artifacts. Such processing may be performed in accordance with conventional CT reconstruction. This artifact only image is then scaled and subtracted from the original image to produce a partial volume corrected image. The partial volume corrected image is then displayed, for example, on display 42 (FIG. 2).

The above-described algorithm is described in connection with an axial scan. The algorithm may also be used in connection, for example, with a helical scan. In connection with a helical scan, overlapped images can be generated without additional data acquisition, and it is believed that a gradient image can be generated in finer steps. For example, if an axial scan is performed with 10 mm collimation, adjacent slices may be obtained approximately 5 mm apart. However, with a 1:1 pitch helical scan, wherein the table increments 10 mm per table rotation, images may be generated approximately 1 mm apart. Accordingly, it is believed that generating gradient images with helical scanning might provide an improved estimation of partial volume artifacts.

The above-described algorithm estimates partial volume artifacts by squaring the gradient image projections. However, higher orders of correction, i.e., cubing, or quintupling, may also be used. Similarly, parameters, such as image size, number of views in a projection, and size of the projections, may be modified to provide a trade-off between computational efficiency and accuracy of partial volume artifact estimation.

The above-described algorithm removes partial volume artifacts by processing the gradient image projections to generate an "artifact only" image, then subtracting the "artifact only" image from an original image. However, and in accordance with another embodiment of the present invention, partial volume artifacts may be removed from original projection data, rather than from an original image. Particularly, the squared gradient image projections are scaled and subtracted from an original projection to generate substantially "artifact free" projection data. Such "artifact free" projection data is then processed to generate a partial volume corrected image which is displayed, for example, on display 42 (FIG. 2).

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, although the CT system described herein is a "third generation" system, many other systems, such as "fourth generation" systems may be used. In addition, the algorithm described herein was implemented in connection with a helical scan, however the algorithm may also be implemented in connection with a helical scan. Furthermore, while the threshold identified herein was 200 HU, other threshold may be used. Accordingly, the spirit and scope of the invention are to be limited only by the terms of the appended claims.

What is claimed is:

1. A method for reducing partial volume artifacts in scan data of an object, the scan data collected in a tomographic scan, said method comprising the steps of:

estimating an attenuation variation of the object; and estimating partial volume errors using the estimated attenuation variation.

2. A method in accordance with claim 1 further comprising the step of removing the estimated partial volume errors from the scan data of the object.

3. A method in accordance with claim 2 wherein removing the estimated partial volume errors comprises the step of generating an artifact only image.

4. A method in accordance with claim 1 wherein estimating the attenuation variation of the object comprises the steps of:

scanning the object to obtain projection data for at least two slices of the object;

process the obtained projection data to generate image data for at least two slices;

filtering the generated image data for the slices; and generating a gradient image.

5. A method in accordance with claim 4 wherein filtering the generated image data comprises the step of segmenting the generated image data into low attenuation image data and high attenuation image data.

6. A method in accordance with claim 5 wherein segmenting the generated image data is performed using greyscale thresholding.

7. A method in accordance with claim 4 wherein scanning the object is performed with an axial scan.

8. A method in accordance with claim 4 wherein scanning the object is performed with a helical scan.

9. A method in accordance with claim 4 wherein estimating partial volume errors comprises the steps of:

forward projecting the gradient image; and squaring the forward projected gradient image.

10. A system for reducing partial volume artifacts in scan data of an object, the scan data collected in a tomographic scan, said system configured to:

estimate an attenuation variation of the object; and estimate partial volume errors using the estimated attenuation variation.

11. A system in accordance with claim 10 further configured to remove the estimated partial volume errors from the scan data of the object.

12. A system in accordance with claim 11 wherein to remove the estimated partial volume errors, said system is configured to generate an artifact only image.

13. A system in accordance with claim 10 wherein to estimate the attenuation variation of the object, said system is further configured to:

scan the object to obtain projection data for at least two slices of the object;

process the obtained projection data to generate image data for at least two slices;

filter the generated image data for the slices; and generate a gradient image.

14. A system in accordance with claim 13 wherein to filter the generated image data, said system is configured to segment the generated image data into low attenuation image data and high attenuation image data.

15. A system in accordance with claim 13 wherein said system is configured to perform an axial scan.

16. A system in accordance with claim 13 wherein said system is configured to perform a helical scan.

17. A system in accordance with claim 13 wherein to estimate partial volume errors, said system is further configured to:

forward project the gradient image; and square the forward projected gradient image.

18. A system for producing a tomographic image of an object from scan data of the object, said system comprising an x-ray source and a detector, said detector having a plurality of detector cells, said system removing partial volume artifacts from the scan data of the object and configured to:

estimate an attenuation variation of the object; and estimate partial volume errors using the estimated attenuation variation.

19. A system in accordance with claim 18 wherein to estimate the attenuation variation of the object, said system is further configured to:

scan the object to obtain projection data for at least two slices of the object;

process the obtained projection data to generate image data for at least two slices;

filter the generated image data for the slices; and generate a gradient image.

20. A system in accordance with claim 19 further configured to perform axial scan.

* * * * *